(12) United States Patent
Hoffmann

(10) Patent No.: US 6,220,451 B1
(45) Date of Patent: Apr. 24, 2001

(54) LABORATORY PRIMARY SAMPLE DISTRIBUTOR WITH DISTRIBUTING DEVICE

(75) Inventor: Uwe Hoffmann, Olfen (DE)

(73) Assignee: Olympus Diagnostica GmbH, Hamburg (DE)

( * ) Notice: Subject to any disclaimer, the term of this patent is extended or adjusted under 35 U.S.C. 154(b) by 0 days.

(21) Appl. No.: 09/302,276

(22) Filed: Apr. 30, 1999

(30) Foreign Application Priority Data

May 4, 1998 (DE) .............................. 198 19 812

(51) Int. Cl.⁷ ................................. G01N 35/00
(52) U.S. Cl. .................. 209/522; 209/524; 209/583; 422/65
(58) Field of Search .................. 209/576, 583, 209/522, 524; 422/65

(56) References Cited

U.S. PATENT DOCUMENTS

| | | | |
|---|---|---|---|
| 4,315,891 | * | 2/1982 | Sakurada ............................ 422/65 X |
| 5,151,184 | * | 9/1992 | Ferkany ............................... 210/514 |
| 5,350,564 | * | 9/1994 | Mazza et al. ....................... 422/65 X |
| 5,362,648 | * | 11/1994 | Koreyasu et al. ................... 422/65 X |
| 5,623,415 | * | 4/1997 | O'Bryan et al. ................... 422/65 X |
| 5,876,670 | * | 3/1999 | Mitsumaki et al. .................... 422/65 |
| 5,972,295 | * | 10/1999 | Hanawa et al. ....................... 422/65 |
| 6,060,022 | * | 5/2000 | Pang et al. ............................ 422/65 |

FOREIGN PATENT DOCUMENTS

| | | |
|---|---|---|
| 25 01 154 | 8/1975 | (DE) . |
| 35 12 459 | 10/1986 | (DE) . |
| 37 00 654 | 7/1988 | (DE) . |
| 43 19 061 | 12/1993 | (DE) . |
| 44 10 781 | 10/1994 | (DE) . |
| 296 08 120 | 9/1996 | (DE) . |

OTHER PUBLICATIONS

Boehringer Mannheim brochure, "PPV 1200, Das Primär Proben Verteilersystem für den präanalytischen Bereich", 4 unnumbered pages, date stamped Apr. 26, 1996 (in German).
Japanese Patent Abstract 07236838 A, Date of Publication Dec. 9, 1995, Method for Centrifugal Separation Treatment of Specimen And Apparatus Therefor.
Ismatec ASA (Analytische System–Apparate), p. 21, ASA–System Zur Kontrolle der Wirkstoffverteilung Tabletten.
English note for DE 296 08 120 U1.
English note for DE 25 01 254.
English note for DE 35 12 459.
English note for DE 37 00 654.
English note for DE 43 19 061.
English note for Brochure PPV 1200.

* cited by examiner

*Primary Examiner*—Steven A. Bratlie
(74) *Attorney, Agent, or Firm*—Rankin, Hill, Porter & Clark LLP

(57) ABSTRACT

A laboratory primary sample distributor equipped with a sorter device removing receptacles containing lab samples fitted with destination coding and arriving on a conveyor belt after having code-reading, and with a sorter gripper that transfers the receptacles into one of several destination transport means intended for different destinations. The sorter gripper is designed to simultaneously pick up several receptacles.

6 Claims, 1 Drawing Sheet

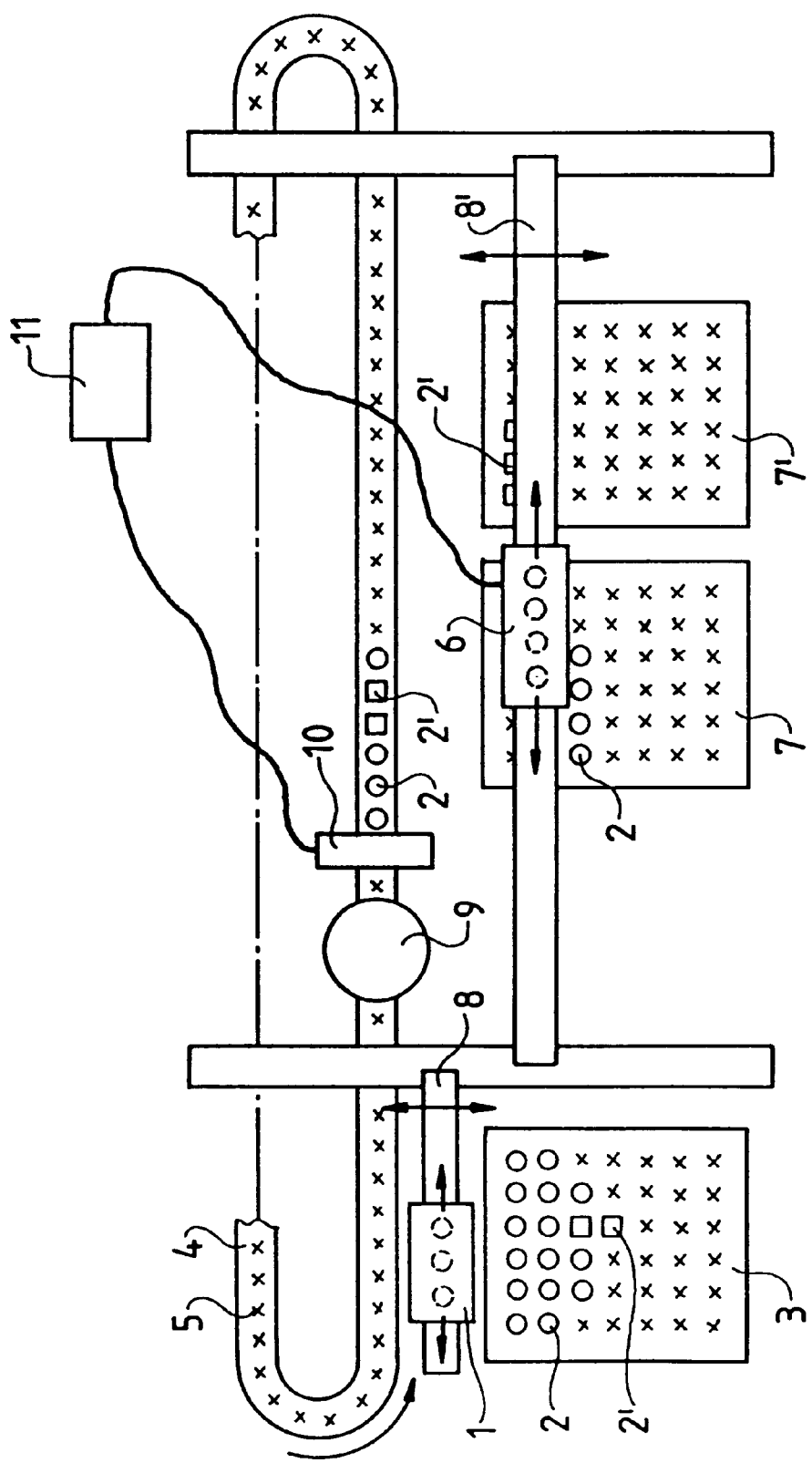

LABORATORY PRIMARY SAMPLE DISTRIBUTOR WITH DISTRIBUTING DEVICE

FIELD OF THE INVENTION

The invention relates to a laboratory primary sample feeder or distributor (hereafter primary distributor) with a distributor or sorter device for removing coded receptacles containing lab samples arriving on a conveyor belt and, from this belt after code-reading, transferring the samples with a sorter gripper into one of several destination transport means intended for different destinations in accordance with the codes.

BACKGROUND OF THE INVENTION

Medical labs receive from physicians samples of blood, serum, urine and other body fluids in receptacles, accompanied by their particular labels on which the desired tests, for instance, blood sugar, AIDS and the like, are checked off. Typically the receptacles are small tubes and they are also used in lab work. They are coded, for instance, by means of stick-on labels to be fed into a computer together with the test requirements.

The receptacles are placed into input magazines wherein they are configured, for instance, in rows in racks or in a planar array in trays, the trays optionally also being furnished with several racks. The receptacles are upright in these input magazines in which they are first moved to a primary distributor. The task of this primary distributor is to read the code of every incoming receptacle, to interrogate the computer about the desired test, and then to place each receptacle, by means of a sorter device, on one or several destination transport means that move the receptacles to individual analyzers for the different tests. In turn, the destination transport means may be magazines, for instance trays, by means of which the receptacles are manually moved from the primary distributor to the analyzers. However, they also may be conveyor belts in which, in their erect position or, if called for in magazines, they are moved, for instance, to a high-output analyzer in high demand.

A primary distributor of this type is known from German patent document 296 08 120 U1. The receptacles are moved in racks to this primary distributor and then, while in these racks, they are placed on a conveyor belt moving the receptacles through a device opening their seals, through a read unit and to a sorter device wherein the receptacles are removed by a sorter gripper from the racks on the conveyor belt and are transferred as required into the particular destination trays.

These known primary distributors incur the drawback that the sorter gripper transports only one receptacle at a time. This sorter gripper must grip each receptacle individually from the conveyor belt, move it to the particular destination tray, deposit it on the tray, and move back. Because of the substantial distances it must cover, its output is intrinsically limited.

SUMMARY OF THE INVENTION

An object of the present invention is to create a primary distributor having higher output.

In accordance with the invention, the sorter gripper can move several receptacles simultaneously. Illustratively, when its receptacle-support geometry coincides with the receptacle array on the conveyor belt, the sorter gripper can pick up several receptacles in one operation and move them jointly into the set-up zone of the destination transport means, for instance trays. This procedure saves time. By means of the destination trays, the sorter gripper next can deposit the receptacles into the desired trays and, as a result, a substantial overall saving in motion is achieved and the output is increased. The controlling computer system can be fed with path-optimizing algorithms. The output is further increased thereby.

Grouped by destination, the receptacles can be moved on the conveyor belt of the primary distributor to the sorter device. Thereupon, they can always be received in sets by the sorter gripper and be deposited into the associated destination tray. Typically, however, the receptacles arrive at the lab mixed with others having different destinations. To solve this, the receptacles can be retrieved according to destination from the conveyor belt and also can be individually deposited into destination transport means such as trays or conveyor belts that continue. Therefore, receptacles with different destinations can be transferred in one operation in the sorter gripper.

The sorter gripper can be moved in a controlled manner toward those receptacles on the conveyor belt of the primary distributor which are intended for a given destination transport means, that is for a certain tray. Thereupon, these receptacles can be deposited in one operation into this tray. With this method, the gripper only has to move over smaller paths over the conveyor belt to pick up receptacles of the same destination instead of having to move over longer paths between the intrinsically spaced destination transport means to distribute receptacles of different destinations between them. As a result, the overall path is substantially optimized and the output is significantly raised.

BRIEF DESCRIPTION OF THE DRAWINGS

The drawing illustratively and schematically shows a top plan view of a much simplified primary distributor in accordance with the invention.

DESCRIPTION OF THE PREFERRED EMBODIMENT

Receptacles 2, 2' are upright in a tray 3 and are moved toward a transfer gripper 1 of the shown primary distributor. Illustratively, tray 3 may be set on a table, not shown. Receptacles 2, 2' are held in receptacle seats or recesses in tray 3. Empty receptacle seats are denoted by crosses. In the shown embodiment, receptacles 2, 2' are to be subjected to two different tests, for instance a blood sugar test and an AIDS test. To distinguish these receptacles 2, 2' in the Figure, they are shown with different contours, namely, blood-sugar test receptacles 2 are shown as having a circular cross-section and the AIDS test receptacles 2' are shown as having a square one. This notation, of course, is solely for purposes of illustration. As a rule the receptacles are identical in shape, for instance of the conventional tubular form.

The transfer gripper 1 is supported displaceably on an x-y rail system schematically shown at 8 above the surface of tray 3 and it may be designed to pick up receptacles individually or several simultaneously. In this embodiment, it is designed to pick up three receptacles. Suitable seats, for instance grippers, are indicated by dashed lines. After picking up the receptacle(s), transfer gripper 1 moves above a conveyor belt 4 having recesses or seats 5 into which this gripper deposits the previously picked-up receptacles 2, 2'. Empty seats 5 are denoted by crosses on conveyor belt 4. The details of the gripper are not shown because such grippers are known and can be selected from conventional designs. In the apparatus of the invention, the gripper in each gripping place may have the conventional jaws or tongs as gripping means, gripping the receptacles from above.

Conveyor belt 4 moves receptacles 2, 2' through an opening apparatus 9 which opens the receptacles by pulling out stoppers, by unscrewing screw caps, or the like, and, where called for, rotating them into a desired reading position. The codes on the receptacles are read by a reading system 10 and the data are fed into the computer 11 which controls the primary distributor.

Thereupon, the receptacles 2,2' arrive in the transfer zone of a sorter gripper 6 which, in the highly schematic illustrative drawing, is displaceable by means of an x-y rail displacement apparatus 8' across a sorting zone.

Sorter gripper 6 is designed to pick up and hold several receptacles 2, 2' and, in the embodiment shown, it can pick up and deposit these receptacles one or several at a time. In this embodiment, sorter gripper 6 includes four holders indicated by dashed lines. As shown in this Figure by means of an electrical cable, the displacement of sorter gripper 6 is controlled by computer 11 of the primary distributor, path-optimizing algorithms being used if desired.

The Figure shows a total of six already scanned receptacles 2, 2' on conveyor belt 4 which have passed reading system 10 and intended for the two previously mentioned different tests for blood sugar (2) and AIDS (2'). These receptacles are to be transferred by sorter gripper 6 onto two destination trays 7, 7' which are within the displacement range of gripper 6, namely destination tray 7 to receive the receptacles 2 and destination tray 7' to receive receptacles 2', in order to then allow moving destination tray 7 to a blood-sugar analyzer and destination tray 7' to an AIDS analyzer. Illustratively, destination trays 7,7' rest on a table, not shown. They are shown partly filled with receptacles 2, 2'. Empty receptacle seats are denoted by crosses.

Sorter gripper 6 in the embodiment shown is designed to pick up as many as four receptacles in one row and, in one simple operational procedure, to pick up all four receptacles 2, 2' from conveyor belt 4 in one simple operational step, and, after moving above destination trays 7, 7', to deposit these receptacles individually therein on destination, into empty tray seats and according to destination.

In a preferred operational mode, the sorter gripper moves above and along the conveyor belt 4 and initially only picks up the receptacles 2 which are to go to the destination tray 7. This gripper can pick up sequentially all four receptacles 2 and then move them jointly in one displacement step above tray 7 and deposit them jointly in one row. Thereupon the gripper moves back and picks up receptacles 2' to move them to destination tray 7'. In this manner the displacement paths are minimized and the sorting output is optimized.

Other ways of optimizing the motions are conceivable, depending in part also on the form of the destination transport means. In the embodiment shown, the destination transport means are in the form of rectangular destination trays 7, 7'. Regarding special analyzers, appropriate rotary magazines may be used, also continuing belts to further convey the receptacles and passing through the displacement range of the sorter gripper 6 wherein they then are loaded. Corresponding control programs stored in computer 11 may be used for path optimization for such different destination transport means.

What is claimed is:

1. A laboratory primary sample distributor comprising:
    conveyor means for delivering encoded sample receptacles containing lab samples;
    means for reading a code from said receptacles;
    a sorting device for removing said receptacles (2, 2') from said conveyor means after code reading and transferring said receptacles (2, 2') into respective destination transport means (7, 7'), each of said respective destination transport means being intended for different destinations, said sorting device including a sorter gripper (6), said sorter gripper including means for picking up receptacles individually, simultaneously holding a plurality of receptacles (2, 2'), and depositing receptacles (2, 2').

2. A laboratory primary sample distributor as claimed in claim 1, wherein said sorter gripper (6) is controlled as a function of said coding of said receptacles (2, 2') resting on the conveyor means (4) in the range of action of said sorter gripper so that, in one transfer step, said sorter gripper sequentially travels to several receptacles (2') intended for a selected destination transport means, grips said receptacles and moves said receptacles simultaneously to said selected destination transport means.

3. A laboratory primary sample distributor as claimed in claim 1, wherein said receptacles are deposited individually.

4. A laboratory primary sample distributor as claimed in claim 3, wherein said sorter gripper (6) is controlled as a function of said coding of said receptacles (2, 2') resting on the conveyor means (4) in the range of action of said sorter gripper so that, in one transfer step, said sorter gripper sequentially travels to several receptacles (2') intended for a selected destination transport means, grips said receptacles and moves said receptacles simultaneously to said selected destination transport means.

5. A laboratory primary sample distributor comprising:
    conveyor means for delivering encoded sample receptacles containing lab samples;
    means for reading a code from said receptacles;
    a sorting device for removing said receptacles (2, 2') from said conveyor means after code reading and transferring said receptacles (2, 2') into a respective destination transport means (7, 7'), each of said respective destination transport means being intended for different destinations, said sorting device including a sorter gripper (6), said sorter gripper including means for picking up receptacles (2, 2'), simultaneously holding a plurality of receptacles (2, 2'), and depositing receptacles individually.

6. A laboratory primary sample distributor according to claim 5, wherein said sorter gripper (6) is controlled as a function of said coding of said receptacles (2, 2') resting on the conveyor means (4) in the range of action of said sorter gripper so that, in one transfer step, said sorter gripper grips a first selected receptacle intended for a first selected destination transport means and grips a second selected receptacle intended for a second selected destination transport means, said sorter gripper then sequentially delivers said first selected receptacle to the first selected destination transport means and then delivers the second selected receptacle to the second selected destination transport means.

* * * * *